United States Patent [19]

Gharib

[11] Patent Number: 5,220,920
[45] Date of Patent: Jun. 22, 1993

[54] ELECTROCHEMICAL MEASUREMENT SYSTEM HAVING INTERFERENCE REDUCTION CIRCUIT

[75] Inventor: James Gharib, San Diego, Calif.

[73] Assignee: Via Medical Corporation, San Diego, Calif.

[21] Appl. No.: 790,669

[22] Filed: Nov. 8, 1991

[51] Int. Cl.$^5$ .............................................. A61B 5/00
[52] U.S. Cl. .................................... 128/635; 204/403
[58] Field of Search ............... 128/635, 696, 901, 673; 204/403

[56] References Cited

U.S. PATENT DOCUMENTS

| | | |
|---|---|---|
| H516 | 9/1988 | Lattin et al. . |
| 3,820,392 | 6/1974 | Beck et al. . |
| 4,237,878 | 12/1980 | Kobayashi et al. . |
| 4,243,045 | 1/1981 | Maas . |
| 4,248,086 | 2/1981 | Zizine . |
| 4,363,244 | 12/1982 | Rabeh et al. . |
| 4,700,709 | 10/1987 | Kraig ..................... 128/635 |
| 4,887,609 | 12/1989 | Cole, Jr. . |
| 4,899,760 | 2/1990 | Jaeb et al. . |

Primary Examiner—Lee S. Cohen
Assistant Examiner—Marianne Harley
Attorney, Agent, or Firm—Pretty, Schroeder, Brueggemann & Clark

[57] ABSTRACT

A system for electrically measuring certain chemical characteristics of electrically-conductive fluids, such as blood, located within a tube and subject to electrical current interference. The measurements are made by measuring the voltage potential between a reference electrode and a sensor electrode sensitive to a particular blood parameter such as pH or calcium, potassium or chloride concentration. A bypass path for the electrical current interference is provided by a pair of noise-reduction electrodes located on opposite sides of the reference and sensor electrodes and interconnected by an amplifier having a relatively low output impedance and a relatively high input impedance. The electrical current interference bypasses the signal electrodes by flowing directly into the amplifier's output terminal, such that the reference and sensor electrodes develop a potential between them that is independent of the electrical current interference.

12 Claims, 1 Drawing Sheet

ELECTROCHEMICAL MEASUREMENT SYSTEM HAVING INTERFERENCE REDUCTION CIRCUIT

BACKGROUND OF THE INVENTION

This invention relates generally to systems for electrically measuring certain chemical characteristics of fluids, e.g., concentration of certain analytes such as ions, gases and metabolites in human blood, and, more particularly, to electrical circuits for reducing the effects of electrical interference in such measurement systems.

Systems of this general kind can take the form of blood chemistry diagnostic systems integrated into infusion fluid delivery systems of the kind commonly used in hospital patient care. Such fluid delivery systems infuse nutrients, medications and the like directly into the patient at a controlled rate and in precise quantities for maximum effectiveness. Infusion fluid delivery systems are connected to a patient at an intravenous (IV) port, in which a hollow needle/catheter combination is inserted into a blood vessel of the patient and thereafter an infusion fluid is introduced into the vessel at a controlled rate, typically using a peristaltic pump. Blood chemistry monitoring systems that are combined with infusion delivery systems of this kind use the IV port to periodically withdraw a blood sample, perform measurements of blood ion concentrations and the like, and then discard the blood or reinfuse it into the patient. The system then resumes delivery of the infusion fluid.

Such combined infusion fluid delivery and blood chemistry monitoring systems include an infusion line and catheter through which the infusion fluid is provided to the patient and blood samples are withdrawn. The infusion line incorporates an electrode assembly having electrochemical sensors that are periodically exposed to the blood samples and thereby provide electrical signals to an analyzer for conversion into corresponding blood chemistry data. A control unit periodically halts delivery of the infusion fluid for a brief interval, during which time a blood sample is withdrawn from the patient into the infusion line and routed to the electrode assembly, which then generates the electrical signals. After the electrical signals have been received by the analyzer, the control unit disposes of the blood or reinfuses it into the patient, and the flow of infusion fluid is resumed.

The electrode assembly typically includes a reference electrode and a plurality of sensor electrodes that are each sensitive to a particular ion of interest. All of the electrodes are embedded in the base of the electrode assembly. Electrochemical sensors generate electrical signals, either a voltage or a current, only in response to contact with the particular species to which they are sensitive, and therefore provide selective measurement of the amount of that species in the blood. Sensor electrodes can be provided to measure, for example, partial pressure of oxygen ($pO_2$) and carbon dioxide ($pCO_2$), glucose, calcium, hydrogen ion, chloride, potassium, and sodium.

The accuracy of the measurements described above can be adversely affected by any electrical current interference, usually originating at the patient, that is conducted along the infusion tube by the blood and the infusion fluid. Appropriate low-pass filtering of the electrical potential measurements can reduce the effects of this noise; however, substantial inaccuracies remain. Movement of the infusion tube relative to the patient provides even greater noise and makes the task of filtering or otherwise reducing the effects of the noise even more difficult.

It should therefore be appreciated that there is a need for an electrochemical measurement system of this particular kind that is less susceptible to interference from electrical current noise being conducted along the fluid line. The present invention fulfills this need.

SUMMARY OF THE INVENTION

This invention resides in an apparatus, and related method, for measuring a predetermined parameter of an electrically-conductive fluid located in a tube, which are effective in substantially eliminating the adverse effects of any electrical current interference being conducted along the tube from a noise source at one end of the tube. The apparatus and method are particularly useful as part of an infusion delivery system, in analyzing of blood chemistry.

More particularly, the apparatus includes an electrode assembly having a reference electrode and a plurality of sensor electrodes located at spaced-apart locations along a fluid path, along with signal amplifier means for sensing the voltage between the reference electrode and each sensor electrode and for providing a corresponding voltage signal indicative of a predetermined parameter of the contained fluid, for which the particular sensor is sensitive. The sensor electrodes can include ion-selective electrodes and other types of electrochemical sensors. First and second noise-reduction electrodes also are located in the electrode assembly, on opposite sides of the reference and sensor electrodes. A noise-reduction amplifier having an input terminal with a high impedance and an output terminal with a low impedance is connected between the first and second noise-reduction electrodes, with its input terminal connected to the electrode furthest from the noise source and with its output terminal connected to the electrode closest to the noise source. Electrical current interference thereby is diverted through the noise-reduction amplifier, bypassing the portion of the infusion tube where the reference and sensor electrodes are located. The voltage signals produced by the signal amplifier means thereby are substantially unaffected by that electrical current interference.

In other, more detailed features of the invention, the noise-reduction amplifier takes the form of an operational amplifier with its negative input terminal connected to the noise-reduction electrode located furthest from the noise source and with its positive input terminal connected to a ground reference. The electrical current interference typically is only ac, and the noise-reduction amplifier is operable to bypass the entire bandwidth of the ac current.

Other features and advantages of this invention should become apparent from the following description of the preferred embodiment, taken in conjunction with the accompanying drawings, which illustrate, by way of example, the principles of the invention.

DESCRIPTION OF THE PREFERRED EMBODIMENT

The following description of the preferred embodiment of the invention is not to be taken in a limiting sense, but is made merely for the purpose of illustrating the general principles of the invention. The description is of the best mode presently contemplated for carrying out the invention.

Figure 1:
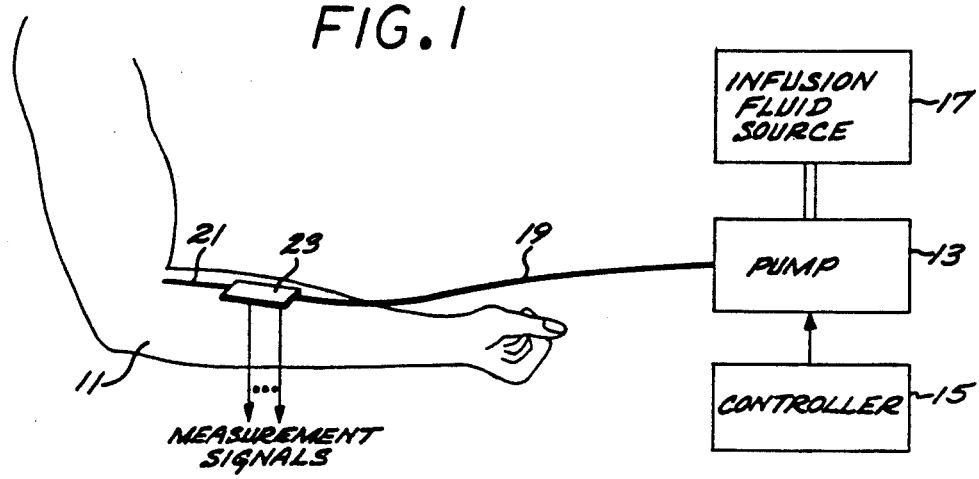
FIG. 1 is a schematic diagram of a combination infusion fluid delivery and blood chemistry analysis system in accordance with a preferred embodiment of the invention, shown being coupled to the arm of a patient.

With reference to FIG. 1, there is shown an infusion fluid delivery and blood chemistry analysis system in use connected to the arm 11 of a patient. An infusion pump 13, under the control of a controller 15, pumps an infusion fluid from a fluid source 17 to a blood vessel in the patient's arm via an infusion tube 19 and hollow needle 21. An electrode assembly 23 is located in the middle of the infusion line and arranged such that the infusion fluid passes through it on its way to the patient.

Periodically, the controller 15 conditions the pump 13 to interrupt its pumping of the infusion fluid to the patient and, instead, to reverse direction and draw a blood sample from the patient. This blood sample is drawn rearwardly through the infusion tube 19 as far as the electrode assembly 23, to allow the assembly to measure certain characteristics of the blood. After the measurements have been completed, the pump reinfuses the blood sample back into the patient, and then resumes pumping the infusion fluid.

Figure 2:
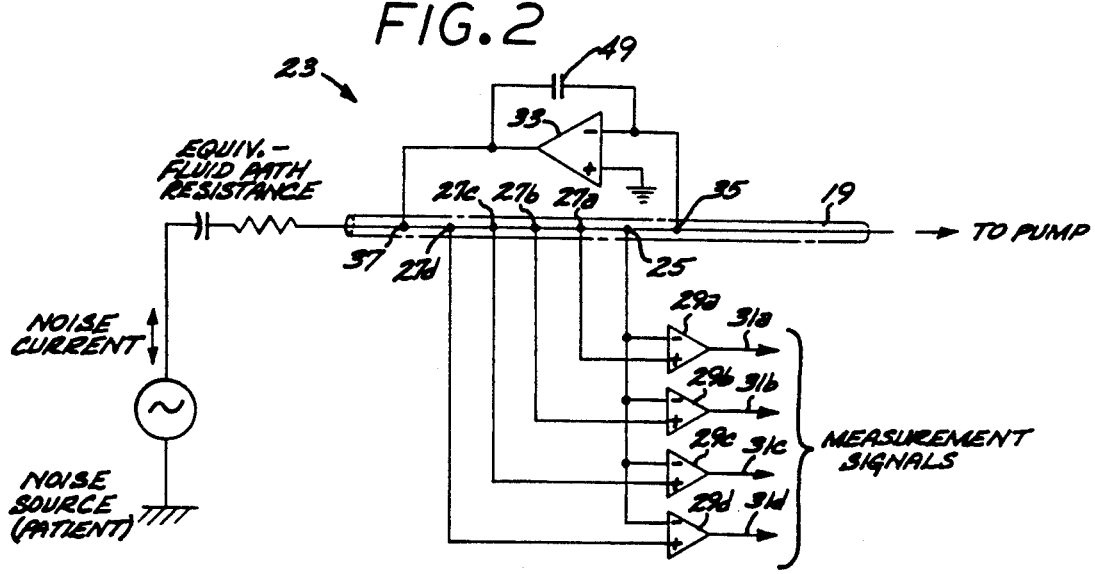
FIG. 2 is a schematic circuit diagram of an electrode/amplifier assembly having a noise-reduction circuit, the assembly being part of the analysis system of FIG. 1.

The electrode assembly 23 is depicted in greater detail in FIG. 2. It includes a single reference electrode 25 and four separate sensor electrodes 27a-27d located at spaced location along the fluid flow path and arranged to contact the fluid flowing through it. Each of the sensor electrodes includes an electrochemical sensor and it is adapted to develop between it and the reference electrode a voltage potential that varies in accordance with a predetermined parameter of the adjacent fluid to which the electrochemical sensor is sensitive. Examples of parameters that are commonly measured in this fashion include pH, concentrations of sodium, potassium and calcium, and glucose, hematocrit, and partial pressures of oxygen ($pO_2$) and carbon dioxide ($pCO_2$). Amplifiers 29a-29d are arranged to amplify the differential voltages provided by the reference electrode and the respective sensor electrodes 27a-27d, to provide amplified measurement signals for output on lines 31a-31d.

In blood chemistry analysis systems like that depicted in FIG. 1, it is known that electrical interference in the form of an undesired electrical current can originate at the patient and be conducted along the infusion tube 19 by the contained fluid, i.e., infusion fluid and/or blood, and thus can interfere with the potential measurements being made. This electrical current interference has only ac components and is affected substantially by movement of the patient and/or the infusion tube. The current affects the voltage potential measurements in accordance with the inherent resistivity of the fluid(s) located between the reference electrode 25 and each sensor electrode 27a-27d.

In accordance with the invention, a bypass path for the electrical current interference is provided by an operational amplifier 33 connected between first and second noise-reduction electrodes 35 and 37, respectively, situated on opposite sides of the reference electrode 25 and the plurality of sensor electrodes 27a-27d. One suitable form for the electrode assembly is described in detail in copending, commonly-assigned U.S. patent application Ser. No. 07/581,803, filed in the name of David K. Wong and entitled "Electrochemical Sensor Apparatus and Method," which is incorporated by reference. In particular, the operational amplifier's negative, or inverting, input terminal is connected to the noise-reduction electrode 35 located furthest from the patient, while the amplifier's output terminal is connected to the noise-reduction electrode 37 located closest to the patient. The amplifier's positive, or non-inverting, input terminal is connected to a ground reference.

As is conventional, the operational amplifier 33 has a relatively high input impedance that is many orders of magnitude greater than its relatively low output impedance. Consequently, noise currents originating at the patient and flowing along the electrically-conductive fluid in the infusion tube 19 to the electrode assembly 23 are readily diverted to the operational amplifier's output terminal, which functions much like a current sink. The current thereby is precluded from flowing along the fluid located between each signal electrode 27a-27d and the reference electrode 25. The voltage measurements made between these electrodes thereby are substantially unaffected by this electrical current interference originating at the patient.

The noise-reduction electrodes 35 and 37 can be of any suitable construction. Preferably, the first noise-reduction electrode 35 takes the form of a bare silver, silver-plated steel, or stainless steel pin in direct contact with the infusion fluid. The second noise-reduction electrode 37 may be of similar construction or may take the form of an ion-sensitive electrode, e.g., a sodium-sensitive electrode, like the sensor electrodes 27a-27d.

Figure 2A:
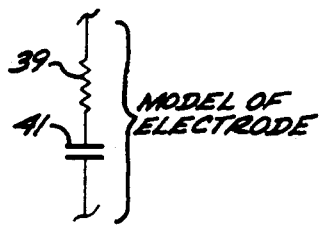
FIG. 2A is a schematic circuit diagram of one equivalent circuit for each electrode in the electrode/amplifier assembly of FIG. 2.

The reference electrode 25, the sensor electrodes 27a-27d, and the noise-reduction electrodes 35 and 37 typically are considered to have an equivalent electrical circuit in the form of a resistor 39 in series with a battery 41 of specified voltage. This is depicted in FIG. 2A.

Figure 2B:
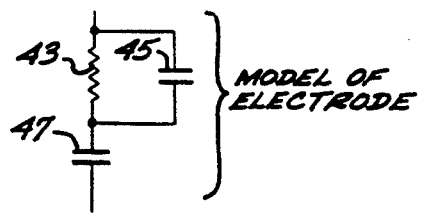
FIG. 2B is a schematic circuit diagram of an alternative equivalent circuit for each electrode in the electrode/amplifier assembly of FIG. 2.

The electrodes alternatively can be considered to have more complex equivalent circuits such as a parallel combination of a resistor 43 and capacitor 45 in series with a battery 47, as depicted in FIG. 2B.

In the case of the reference electrode and sensor electrodes 27a-27d, the batteries in the equivalent circuits yield dc voltage differences that are amplified by the amplifiers 29a-29d. The electrical current flowing through the electrodes is negligible, so the electrode resistance is of minimal significance. Further, the dc voltage differences provided by the noise-reduction electrodes 35 and 37 are of no concern, because the noise-reduction circuit functions merely as a bypass path for ac electrical current interference originating at the patient. A feedback capacitor 49 for the operational amplifier 33 limits the circuit's ac bandwidth to an appropriate range, to overcome the bandwidth of the noise signal.

It should be appreciated from the foregoing description that the present invention provides an improved system for electrically measuring certain chemical characteristics of electrically-conductive fluids such as blood located within a tube and subject to electrical current interference. The measurements are made by measuring the voltage potential between a reference electrode and a sensor electrode located in the fluid line. A bypass path for the electrical current interference is provided by a pair of noise-reduction electrodes that are located on opposite sides of the reference and sensor electrodes and interconnected by an amplifier having a relatively low output impedance and a relatively high input impedance. In particular, the electrical current interference flows directly into the amplifier's output terminal, thereby ensuring that the reference and sensor electrodes develop a potential between them that is independent of the interference. Noise reductions on the order of 120 db are readily achievable.

Although the invention has been described in detail with reference to the presently preferred embodiment, those of ordinary skill in the art will appreciate that various modifications can be made without departing from the invention. Accordingly, the invention is defined only by the following claims.

I claim:

1. Apparatus for measuring a predetermined parameter of an electrically-conductive fluid located in a tube and used in an environment where an undesired electrical current can be conducted by the fluid from a noise source at one end of the tube, the apparatus comprising:

a reference electrode and a sensor electrode adapted to be attached to a tube at spaced-apart locations, contacting an electrically-conductive fluid in the tube;

signal amplifier means for amplifying a voltage between the reference electrode and the sensor electrode and for providing a corresponding amplified signal;

first and second noise-reduction electrodes adapted to be attached to the tube at spaced-apart locations, contacting the electrically conductive fluid in the tube, such that the reference and sensor electrodes are located between the first and second noise-reduction electrodes; and a noise reduction amplifier having an input terminal with a high impedance and an output terminal with a low impedance, the noise-reduction amplifier means being connected between the first and second noise-reduction electrodes, with its input terminal connected to the noise-reduction electrode furthest from the noise source and with its output terminal connected to the noise-reduction electrode closest to the noise source, such that any electrical current originating at the noise source bypasses the portion of the electrically-conductive fluid located in the tube between the reference and sensor electrodes by flowing instead through the noise reduction amplifier, whereby the amplified signal produced by the signal amplifier means is substantially unaffected by that electrical current.

2. Apparatus as defined in claim 1, wherein the noise reduction amplifier includes an operational amplifier having a negative input terminal connected to the noise-reduction electrode that is furthest from the noise source, a positive input terminal connected to a ground reference, and an output terminal connected to the noise-reduction electrode that is closest to the noise source.

3. Apparatus as defined in claim 1, wherein:
the apparatus further includes one or more additional sensor electrodes; and the signal amplifier means include a plurality of amplifiers, each amplifier for amplifying the voltage between the reference electrode and a separate sensor electrode and for providing a corresponding amplified signal.

4. Apparatus as defined in claim 1, wherein:
the noise source generates an ac electrical current having a bandwidth; and
the noise-reduction amplifier to conducts the ac electrical current over the current entire bandwidth.

5. Apparatus as defined in claim 1, wherein the first and second noise-reduction electrodes are pins formed of silver, silver-plated steel, or stainless steel.

6. Apparatus as defined in claim 1, wherein:
the noise-reduction electrode located furthest from the noise source is a pin formed of silver, silver-plated steel, or stainless steel; and
the noise-reduction electrode located closest to -the noise source is sensitive to a predetermined parameter of the electrically-conductive fluid.

7. Apparatus for measuring a predetermined parameter of blood drawn from a patient into an intravenous tube, the apparatus comprising:

a reference electrode and a sensor electrode adapted to be attached at spaced-apart locations in an intravenous tube into which blood can be drawn from a patient to contact the two electrodes, wherein a potential develops between the two electrodes that is indicative of a predetermined parameter of the blood;

wherein electrical current interference originating at the patient can be conducted along the intravenous tube by blood contained in the tube;

first and second noise-reduction electrodes adapted to be attached at spaced-apart locations in the intravenous tube, in contact with blood drawn into the tube, such that the reference and sensor electrodes are located between the first and second noise-reduction electrodes; and a noise reduction amplifier having an input terminal with a high impedance and an output terminal with a low impedance, the noise-reduction amplifier means being connected between the first and second noise-reduction electrodes, with the input terminal connected to the noise-reduction electrode furthest from the patient and with the output terminal connected to the noise-reduction electrode closest to the patient, such that any electrical current originating at the patient bypasses the portion of the tube between the reference and sensor electrodes by flowing instead through the noise reduction amplifier, whereby the potential developed between the reference and sensor electrodes is substantially unaffected by the electrical current.

8. Apparatus as defined in claim 7, wherein the noise-reduction amplifier means includes an operational amplifier having a negative input terminal connected to the noise-reduction electrode that is furthest from the patient, a positive input terminal connected to a ground reference, and an output terminal connected to the noise-reduction electrode that is closest to the patient.

9. Apparatus as defined in claim 7, wherein:
the electrical current noise originating at the patient is an ac current having a bandwidth; and
the noise-reduction amplifier, means is adapted to conduct the ac current over the current's entire bandwidth.

10. Apparatus as defined in claim 7, wherein the first and second noise-reduction electrodes are pins formed of silver, silver-plated steel, or stainless steel.

11. Apparatus as defined in claim 7, wherein:
the noise-reduction electrode located furthest from the noise source is a pin formed of silver, silver-plated steel, or stainless steel; and
the noise-reduction electrode located closest to the noise source is sensitive to a predetermined parameter of the electrically-conductive fluid.

12. A method for measuring a predetermined parameter of blood drawn from a patient into an intravenous tube, the method comprising steps of:
providing an electrode and infusion tube assembly having a reference electrode and a sensor electrode located at spaced apart locations, the sensor electrode being sensitive to a particular parameter of blood;
arranging the electrode and infusion tube assembly such that blood can be drawn from a patient into contact with one or both of the reference and sensor electrodes, wherein a potential develops between the two electrodes that is indicative of the predetermined parameter of the blood, and wherein electrical current interference originating at the patient can be conducted along the infusion tube by the blood contained in the tube; and
connecting a noise-reduction amplifier between two noise-reduction electrodes located on opposite sides of the reference and sensor electrodes, wherein the amplifier has a high-impedance input terminal connected to the noise reduction electrode located furthest from the patient and a low-impedance output terminal connected to the noise reduction electrode closest to the patient, such that any electrical current interference originating at the patient bypasses the reference and sensor electrodes by flowing instead through the noise-reduction amplifier, whereby the potential developed between the reference and sensor electrodes is substantially unaffected by that electrical current.

* * * * *